United States Patent [19]
Coffin et al.

[11] Patent Number: 5,407,687
[45] Date of Patent: Apr. 18, 1995

[54] RANITIDINE SOLID DOSAGE FORM

[75] Inventors: Mark D. Coffin; Alan F. Parr, both of Cary, N.C.

[73] Assignee: Glaxo Inc., Research Triangle Park, N.C.

[21] Appl. No.: 200,045

[22] Filed: Feb. 22, 1994

[51] Int. Cl.⁶ ................................................. A61K 9/24
[52] U.S. Cl. .................................... 424/472; 424/473; 514/926
[58] Field of Search ................... 424/472, 473; 514/926

[56] References Cited

U.S. PATENT DOCUMENTS

| | | | |
|---|---|---|---|
| 4,128,658 | 12/1978 | Price et al. | 424/285 |
| 4,521,431 | 6/1985 | Crookes | 514/471 |
| 4,534,973 | 8/1985 | Kim et al. | 514/162 |
| 4,585,790 | 4/1986 | Padfield et al. | 514/471 |
| 4,786,503 | 11/1988 | Edgren et al. | 424/472 |
| 4,880,636 | 11/1989 | Franz | 424/480 |
| 4,915,954 | 4/1990 | Ayer et al. | 424/472 |
| 4,946,685 | 8/1990 | Edgren et al. | 424/472 |
| 5,028,432 | 7/1991 | Chopra et al. | 414/451 |
| 5,055,306 | 10/1991 | Barry et al. | 424/482 |
| 5,068,249 | 11/1991 | Long | 514/471 |
| 5,102,665 | 4/1992 | Schaeffer | 424/466 |

*Primary Examiner*—Thurman K. Page
*Assistant Examiner*—James M. Spear
*Attorney, Agent, or Firm*—Charles T. Joyner

[57] ABSTRACT

The present invention comprises a bi-layer, pharmaceutical tablet having one layer formulated for the immediate release (IR) of ranitidine and a second layer formulated for sustained release (SR) of ranitidine with the ratio of ranitidine in the IR layer to that in the SR in the range of from about 30:70 to about 60:40.

6 Claims, No Drawings

RANITIDINE SOLID DOSAGE FORM

The present invention relates to pharmaceutical solid dosage forms having an immediate release layer and a slow release layer with each layer containing ranitidine as an active ingredient.

BACKGROUND OF THE INVENTION

The drug ranitidine, chemically identified as N-[2-[[[5-(dimethyl-amino)methyl-2-furany]methyl]thio]ethyl]-N'-methyl-2-nitro-1,1-ethenediamine and its physiologically acceptable salts are described and claimed in U.S. Pat. No. 4,128,658, and a particular crystalline form of ranitidine hydrochloride is described and claimed in U.S. Pat. No. 4,521,431 (both incorporated herein by reference). In both these patents there is reference to formulations for oral administration, which may, for example, be in the form of tablets, capsules, granules powders, solution, syrups, suspensions, or tablets or lozenges for buccal administration. Oral preparations of ranitidine are also disclosed in U.S. Pat. Nos. 4,585,790, 4,880,636, 5,028,432, 5,068,249 and 5,102,665. As used herein the term "ranitidine" refers to both the free base and the pharmaceutically acceptable acid addition salts thereof unless otherwise noted.

Ranitidine is an antagonist to histamine $H_2$ receptors. This drug is widely used in the treatment of duodenal ulcers in humans in the form of the hydrochloride salt. While the drug is generally given orally or by injection, the oral route is preferred. Ranitidine HCl is sold under the trademark Zantac® by Glaxo Inc. of Research Triangle Park, North Carolina.

Recently ranitidine has been approved by the FDA for treatment of esophagitis. The patient suffering with esophagitis is effectively treated by administration of 150 mg of ranitidine four times a day. However, the four times a day dosing regime often leads to poor patient compliance. Studies have shown that patient compliance increases as the dosing regime goes from four times a day to twice or once a day. Therefore, a dosage form that reduces the ranitidine daily dosing regime, while maintaining a stable plasma level of ranitidine, i.e., a sustained release form, would be advantageous.

Clinically acceptable sustained release forms of ranitidine using conventional technology have not heretofore been successful. Ranitidine has 50% absolute bioavailability, and it is only absorbed in the initial part of the small intestine. These properties are not favorable for sustained release delivery means.

Numerous patents teach a sustained drug release system and list ranitidine as a suitable candidate. However, such systems do not allow for the peculiar properties of ranitidine and thus yield less than ideal sustained release formulations. That is, these systems do not allow for the balance that must be made between the amount of the drug immediately released and the amount of time over which the remaining drug in the sustained release (SR) portion is released. For example, if too much ranitidine is present in the immediate release (IR) portion, the result is essentially the same as that obtained with the commercially available tablets, i.e., an immediate release formulation. Conversely, if too little ranitidine is present in the immediate release portion, the resulting formulation exhibits poor bioavailability.

Multi-layer, solid drug formulation have been known in the pharmaceutical art for several years. These formulations usually consisted of coated tablets and pellets or multiple-layer tablets (either bi- or tri-layer tablets). Usually the layers are "built-up" with multiple coatings on a tablet core, a process widely practiced in this art. Examples of the application of multi-layer drug formulation to improve the in vivo activity of a drug are given by Kim, et. al. (U.S. Pat. No. 4534973) and Leslie, S. T., et. al. (Pharmaceutical 2(3), pp. 192–194, 1979). The use of multi-layer drug formulations (either as multiple layer tablets or coated tablets or pellets) have been used to sustain the blood level of various drugs. Examples of these types of systems have been applied to theophylline, phenylpropanolamine, aspirin, and many others. In practically all cases, this approach has been applied to drugs that are well absorbed and drugs that are absorbed throughout the entire gastro-intestinal tract.

SUMMARY OF THE INVENTION

The present invention comprises a pharmaceutical solid dosage form having a first layer with an immediate release property and a second layer with a sustained release property. Each of these layers contains ranitidine, with the ratio of the ranitidine in the first layer to the ranitidine in the second layer being in the range of from about 30:70 to about 60:40 by weight.

Another aspect of the present invention is a method of treatment comprising administering to a patient in need thereof a pharmaceutical solid dosage form of the present invention wherein the total amount of ranitidine is a pharmacologically effective amount.

DETAILED DESCRIPTION OF THE INVENTION

The solid dosage form of the present invention features a balance between immediate release and sustained release of ranitidine which provides a lo significantly more uniform, efficient delivery of ranitidine than oral formulations of ranitidine now available on the market. This dosage form may be used for the same indications as the ranitidine tablets now in clinical use. However, it is especially useful where it is desirable to maintain a sustained, uniform dose of ranitidine for twelve to twenty-four hour with the administration of only one or two doses.

In particular the solid dosage form of the present invention may be in the form of a compressed tablet having at least one layer containing ranitidine formulated for immediate release and at least one layer containing ranitidine formulated for sustained release. The layers may be concentric, laminated in a tablet or in mini-tablets, or beads to be administered in a capsule Conveniently, the present invention may be in the form of a bi-layer tablet.

Ranitidine may be used in the dosage form of the present invention in a total amount of from about 25 to about 800 mg per unit dose, calculated as ranitidine base. In particular, a unit dose of about 100 to about 350 mg, e.g., 150 mg (168 mg as the HCl salt) and 300 mg (336 mg as the HCl salt) may be used.

By employing the oral, solid ranitidine dosage form taught herein a patient suffering with esophagitis, at the discretion of the attending physician, may be treated only once or twice a day rather than four or more time a day with conventional oral dosage forms of ranitidine. The less frequent need for dosing is more convenient and easier for a patient to remember to administer. Thus, dosing compliance is higher than with conventional oral forms of ranitidine.

Ranitidine hydrochloride can be prepared in two crystalline forms, i.e., Form 1 disclosed in U.S. Pat. No. 4,128,658 and Form 2 disclosed in U.S. Pat. No. 4,521,431. While either Form 1, or Form 2, or any other form may be used in the present invention, Form 2 is preferred.

As used herein the term "immediate release" or "IR" means a dosage form that delivers the entirety of its drug content at once after administration for the purpose of providing a rapid rise and fall of drug concentration in the blood stream. The term "sustained release" or "SR" means a dosage form that gradually releases its drug content over a given period of time after administration for the purpose of providing a constant concentration of drug in lo the blood stream. The term "active ingredient" means a drug, e.g., ranitidine. The terms "excipient" or "inactive ingredient" means material added to a solid pharmaceutical formulation to impart certain desirable properties. For example, in the case of a tablet, excipients may be added to moderate dissolution rate, mask a bad taste, or improve appearance of the tablet. The term "matrix" or "matrix system" means the combination of all excipents of a given formulation in which the active drug is incorporated.

In the present invention, in addition to ranitidine, other active ingredients, e.g., other $H_2$ antagonists, antacids and synergizing agents, may be added to the formulations of either or both the IR and SR portions of the solid formulations, e.g., to the IR and SR layers of a tablet. Likewise excipients such as binding, matrixing, disbursing, sweetening, coloring, antioxidizing, protecting and lubricating agents may be added to the formulations of either or both the IR and SR portions, e.g., layers of a tablet. Further, the layers containing active ingredients, separate or in combination, may be overcoated with one or more layers of excipients For example, a tablet containing a IR and SR layer fused together may be overcoated with a layer containing a coloring, antioxidizing and protecting layer.

In particular the IR layer comprises ranitidine, filler such as lactose, matrix agents such as microcrystalline cellulose and croscarmellose sodium, a lubricant such as magnesium stearate, and optionally other excipients and other active ingredients.

In particular the SR layer comprises ranitidine, a matrixing agent such as hydroypropylmethylcellulose, filler such as lactose, a lubricant such as magnesium stearate, and optionally other excipients and other active ingredients.

A particular embodiment of the present invention is a pharmaceutical solid dosage form, e.g., a bi-layer tablet, comprising:

| Ingredient | Ratio to ranitidine (by weight) | |
|---|---|---|
| | from about | to about |
| 1) An IR layer containing ranitidine together with: | | |
| a) microcrystalline cellulose | 1:0.6 | 1:3.3 |
| b) croscarmellose sodium | 1:10 | 1:200 |
| c) magnesium stearate | 1:25 | 1:400 |
| d) other optional excipitents and/or active ingredients[1] | — | — |
| 2) An SR layer containing ranitidine together with: | | |
| a) hydroxypropyl methylcellulose | 1:0.1 | 1:1.3 |
| b) lactose | 1:0.3 | 1:2 |
| c) magnesium stearate | 1:12.5 | 1:100 |
| d) other optional excipitents and/or active ingredients[1] | — | — |

[1]. The ratio of the other excipients to ranitidine in each layer will vary according to the nature of each excipient, but would be in the range of from about 1:1 to about 1:500 by weight. Likewise, the ratio of other active ingredients will vary according to the nature of each active ingredient, but would be in the range of from about 100:1 to about 1:100.

wherein the ratio of ranitidine in the IR layer to ranitidine in the SR layer is in the range of from about 30:70 to about 60:40 by weight. In particular, this ratio is the range of from about 35:65 to about 55:45. A more particular embodiment of the present invention is a bi-layer tablet comprising, 1) an IR layer containing
  a) about 50 to about 200 mg of a ranitidine acid addition salt,
  b) about 60 to about 90 mg of microcrystalline cellulose,
  c) about 1 to about 5 mg of croscarmellose sodium,
  d) about 0.5 to about 2.0 mg of magnesium stearate and
  e) optionally other excipients and/or other active ingredient and 2) a SR layer containing
  a) about 50 to about 200 mg of a ranitidine acid addition salt,
  b) about 150 to about 350 mg of hydroxypropylmethylcellulose,
  c) about 100 to about 150 mg of lactose,
  d) about 2.0 to about 4.0 mg of magnesium stearate and
  e) optionally other excipients and/or other active ingredients.

Specifically in each layer ranitidine is in the form of its hydrochloride salt. The ratio of the amount of ranitidine hydrochloride (calculated on the basis of the free base) in the IR layer to that in the SR layer is in the range of from about 30:70 to about 55:45 by weight. Particularly, the ratio of ranitidine hydrochloride in the IR layer to that in the SR layer is in the range of from about 40:60 to about 55:45. For example, this ratio may be 40:60 to 50:50.

The rate of release of ranitidine from a matrix, i.e., the dissolution profile, is controlled by the rate of diffusion of ranitidine through the matrix. Changes in tablet shape which affect tablet surface area may change the dissolution profile. Thus, one skilled in this art will appreciate that a change in tablet shape may cause a change in surface area which may require some adjustment of the IR:SR ratio to produce the optimum, desired dissolution profile.

The sustained release layer of the pharmaceutical solid dosage form of the present invention delivers its ranitidine content over a four to ten hour period at a nearly constant or zero-order rate. In particular, it delivers ranitidine over a six hour period at a nearly constant or zero-order rate.

The pharmaceutical solid dosage form of this invention may be prepared according to procedures known in the art of pharmacy for preparing multi-layer dosage forms (see, Gunsel W.C. and Dusel R.G. "Compression-Coated and Layer Tablets", In Lieberman, H. A., Lacjman, L., and Schwartz, J. B. (eds.), Pharmaceutical Dosage Forms: Tablets, Vol. 1, Marcel Dekker, pp. 247–284 Inc., New York, 1989). Conveniently, to made a bi-layer tablet blends for the immediate release and sustained release layer are prepared separately. Each blend is then loaded onto a layer press and compressed using standard procedures well known in the art.

EXAMPLES

The following examples illustrate aspects of this invention but should not be construed as limitations. The symbols and conventions used in these examples are consistent with those used in the contemporary pharmacy literature, for example, Pharmaceutical Research.

As used herein the terms "300 mg" and "150 mg" mean the tablet formulation contains 300 mg and 150 mg, respectively, of ranitidine calculated as the free base. Avicel brand of microcrystalline cellulose and Ac-Di-Sol brand of croscarmellose sodium, both supplied by FMC Corporation, 1735 Market Street, Philadelphia, PA. 19103, were used in the following examples.

EXAMPLE 1

"300 mg" Tablet formulation with the IR:SR ratio of 50:50

| Ingredient | Amt/tablet |
| --- | --- |
| Immediate release layer | |
| Ranitidine HCl | 168.0 mg |
| Microcrystalline cellulose | 78.3 mg |
| Croscarmellose sodium | 2.5 mg |
| Magnesium stearate | 1.2 mg |
| Sustained release layer | |
| Ranitidine HCl | 168.0 mg |
| Hydroxypropyl methylcellulose | 300.0 mg |
| Lactose | 129.0 mg |
| Magnesium Stearate | 3.0 mg |
| TOTAL WEIGHT | 850.0 mg |

Sieving of materials

A sufficient quantity of the materials are sieved through the listed screen:

| Ingredient | Screen Size Range |
| --- | --- |
| Ranitidine hydrochloride | 14–40 mesh |
| Hydroxypropyl methylcellulose | 20–60 mesh |
| Microcrystalline cellulose | 20–60 mesh |
| Lactose (monohydrate) | 14–40 mesh |
| Croscarmellose sodium | 14–40 mesh |
| Magnesium stearate | 40–60 mesh |

Powder Mixing

Sustained Release Layer

The ranitidine hydrochloride, lactose (monohydrate) and hydroxypropyl methylcellulose are added to a suitable mixer (i.e. twin shell blender) and blended for approximately 30 minutes. Next, magnesium stearate is added to the above mixture, and the mixture is blended continued for approximately 1 minute.

Immediate Release Layer

The ranitidine hydrochloride, microcrystalline cellulose and croscar-mellose sodium are added to a suitable mixer (i.e. twin shell blender) and blended for approximately 30 minutes. Next, magnesium stearate is added to the above mixture, and the mixture is blended for approximately 1 minute.

Compression of Tablets

Tablets are compressed on a tablet compression machine suitable for producing layer tablets (e.g., Hata press model HT-AP55-3LS supplied by Elizabeth Hata International, Inc. Banco Industrial Park, North Huntington, PA) using the procedure of Gunsel W. C. and Dusel R. G., supra, and applying a pre-compression and main compression forces of approximately 0.3 and 1.5 kg, respectively.

EXAMPLE 2

"150 rag" Tablet, formulation with the IR:SR ratio of 50:50

| Ingredient | Amt/tablet |
| --- | --- |
| Immediate release layer | |
| Ranitidine HCl | 84.0 mg |
| Microcrystalline Cellulose | 78.3 mg |
| Croscarmellose sodium | 2.5 mg |
| Magnesium Stearate | 1.2 mg |
| Sustained release layer | |
| Ranitidine HCl | 84.0 mg |
| Hydroxypropyl methylcellulose | 300.0 mg |
| Lactose | 129.0 mg |
| Magnesium Stearate | 3.0 mg |
| TOTAL WEIGHT | 682.0 mg |

This tablet is prepared by the method of Example 1.

EXAMPLE 3

"300 mg" Tablet formulation with the IR:SR ratio of 40:60

| Ingredient | Amt/tablet |
| --- | --- |
| Immediate release layer | |
| Ranitidine HCl | 134.4 mg |
| Microcrystalline Cellulose | 62.6 mg |
| Croscarmellose sodium | 2.0 mg |
| Magnesium Stearate | 1.0 mg |
| Sustained release layer | |
| Ranitidine HCl | 201.6 mg |
| Hydroxypropyl methylcellulose | 133.0 mg |
| Lactose | 141.9 mg |
| Magnesium Stearate | 3.3 mg |
| TOTAL WEIGHT | 679.8 mg |

This tablet is prepared by the method of Example 1.

We claim:

1. A pharmaceutical solid dosage in the form of laminated bi-layer tablet comprising a first layer with an immediate release property and a second layer with a sustained release property each of said layers containing ranitidine, wherein,
    said first layer contains
        a) about 50 to about 200 mg of ranitidine acid addition salt, calculated as the free base
        b) about 60 to about 90 mg of microcrystalline cellulose,
        c) about 1 to about 5 mg of croscarmellose sodium,
        d) about 0.5 to about 2.0 mg of magnesium stearate and
        e) optionally one or more additional active ingredients; and
    said second layer contains a) about 50 to about 200 mg of ranitidine acid addition salt, calculated as the free base
b) about 150 to about 350 mg of hydroxypropylmethylcellulose,
c) about 100 to about 150 mg of lactose,
d) about 2.0 to about 4.0 mg of magnesium stearate, and
e) optionally one or more additional active ingredients.

2. A pharmaceutical solid dosage in the form of laminated bi-layer tablet comprising a first layer with an immediate release property and a second layer with a sustained release property each of said layers containing ranitidine, wherein;
said immediate release layer contains,
  a) 168 mg of ranitidine hydrochloride,
  b) 78.25 mg of microcrystalline cellulose,
  c) 2.50 mg of croscarmellose sodium, and
  d) 1.25 mg of magnesium stearate, and
a sustained release layer containing
  a) 168 mg of ranitidine hydrochloride,
  b) 300 mg of hydroxypropylmethylcellulose,
  c) 129 mg of lactose,
  d) 3.0 mg of magnesium stearate.

3. A pharmaceutical solid dosage in the form of laminated bi-layer tablet comprising a first layer with an immediate release property and a second layer with a sustained release property each of said layers containing ranitidine, wherein;
said immediate release layer contains,
  a) 84 mg of ranitidine hydrochloride,
  b) 78.25 mg of microcrystalline cellulose,
  c) 2.50 mg of croscarmellose sodium, and
  d) 1.25 mg of magnesium stearate, and
said sustained release layer contains
  a) 84 mg of ranitidine hydrochloride,
  b) 300 mg of hydroxypropylmethylcellulose,
  c) 129 mg of lactose,
  d) 3.0 mg of magnesium stearate.

4. The bi-layer tablet of claim 1 wherein said sustained release layer delivers its ranitidine content over a four to ten hour period at a nearly constant or zero-order rate.

5. The bi-layer tablet of claim 1 wherein said sustained release layer delivers its ranitidine content over a six hour period at a nearly constant or zero-order rate.

6. A method of treatment comprising administering to a patient suffering with esophagitis a pharmaceutical solid dosage in the form of laminated bi-layer tablet comprising a first layer with an immediate release property and a second layer with a sustained release property each of said layers containing ranitidine, wherein,
said first layer contains
  a) about 50 to about 200 mg of ranitidine acid addition salt, calculated as the free base
  b) about 60 to about 90 mg of microcrystalline cellulose,
  c) about 1 to about 5 mg of croscarmellose sodium,
  d) about 0.5 to about 2.0 mg of magnesium stearate and
  e) optionally one or more additional active ingredients; and
said second layer contains
  a) about 50 to about 200 mg of ranitidine acid addition salt, calculated as the free base
  b) about 150 to about 350 mg of hydroxypropylmethylcellulose,
  c) about 100 to about 150 mg of lactose,
  d) about 2.0 to about 4.0 mg of magnesium stearate, and
  e) optionally one or more additional active ingredients.

* * * * *

UNITED STATES PATENT AND TRADEMARK OFFICE
CERTIFICATE OF CORRECTION

PATENT NO. : 5,407,687
DATED : April 18, 1995
INVENTOR(S) : Coffin et al.

It is certified that error appears in the above-identified patent and that said Letters Patent is hereby corrected as shown below:

Column 1, line 11, change ")methyl-2-furany]" to --)methyl-2-furanyl]--.

Column 2, line 7, change "(Pharmaceutical 2(3)" to --(Pharmaceutica 2(3)--.

Column 2, line 43, change "twenty-four hour" to --twenty four hours--.

Column 2, line 63, change "four or more time a day" to --four or more times a day--.

Column 3, line 15, change "in lo the blood stream" to --in the blood stream--.

Column 4, line 67, change "to made" to --to make--.

Column 5, line 60, change "is blended continued" to --is blended continuously--.

Column 6, line 9, change "main compression forces" to --main compression force--.

Column 6, line 13, change ""150 rag"" to --"150 mg"--.

Signed and Sealed this

Twenty-third Day of April, 1996

Attest:

BRUCE LEHMAN

*Attesting Officer*  *Commissioner of Patents and Trademarks*